(12) United States Patent
Haas

(10) Patent No.: US 7,078,062 B2
(45) Date of Patent: Jul. 18, 2006

(54) HOP-BASED UDDER AND TEAT DIPS AND WASHES

(75) Inventor: Gerhard J. Haas, Woodcliff Lake, NJ (US)

(73) Assignee: S.S. Steiner, Inc., New York, NY (US)

(*) Notice: Subject to any disclaimer, the term of this patent is extended or adjusted under 35 U.S.C. 154(b) by 522 days.

(21) Appl. No.: 10/046,897

(22) Filed: Jan. 17, 2002

(65) Prior Publication Data

US 2003/0013773 A1    Jan. 16, 2003

Related U.S. Application Data

(60) Provisional application No. 60/261,857, filed on Jan. 17, 2001.

(51) Int. Cl.
*A61K 36/00* (2006.01)

(52) U.S. Cl. ..................................................... 424/725

(58) Field of Classification Search ................. 424/725
See application file for complete search history.

(56) References Cited

U.S. PATENT DOCUMENTS 4,170,638 A * 10/1979 Owades
5,370,863 A * 12/1994 Barney et al.

FOREIGN PATENT DOCUMENTS

JP    01172332    *    7/1989

* cited by examiner

*Primary Examiner*—Susan D. Coe
(74) *Attorney, Agent, or Firm*—Walter D. Ames

(57) ABSTRACT

A method of sanitizing the udders and teats of dairy cows by applying to them an aqueous solution of a hop compound in a concentration sufficient to kill substantial amounts of pathogens but insufficient to cause substantial trauma to the cows.

8 Claims, No Drawings

HOP-BASED UDDER AND TEAT DIPS AND WASHES

This application claims priority based on Provisional Application No. 60/261,857, filed Jan. 17, 2001.

FIELD OF THE INVENTION

The present application relates generally to compositions and processes for the removal of living pathogens from animal tissue. More specifically, it concerns compositions and processes for sanitizing the udders and teats of dairy cattle.

BACKGROUND OF THE INVENTION

The dairy industry uses washes and dips that maintain the teats and udders of dairy cattle clean and sanitary and thereby prevent mastitis. These preparations are intended to kill microbes pathogenic to the cow and also to mankind, as most of the milk is intended for human consumption. Such dips, washes and sanitizing preparations contain an anti-microbial agent, usually chorine based, as well as a surface active agent and materials to keep the skin of the udder in good condition, such as emollients and soothing materials like glycerin and propylene glycol.

Chlorine based anti-microbial agents present several disadvantages that militate against their use in contact with animal tissue., and particularly the sensitive tissue that makes up the teats and udders of cows. Thus, such chlorine based agents can only be used in limited concentrations to prevent udder and teat injury, and even such lower concentrations, which are thereby limited in their effectiveness as bactericides, may have a tendency to irritate the skin of udders and cause discomfort to the animal during and even after the dip or wash has been completed.

Another problem that arises from the use of chlorine based anti-microbial dips and washes of cows' udders and teats is that subsequent washing of the udders may be incomplete, so that a chlorine residue remains on the udders after a water wash. Such residue can cause irritation of the udder for some period of time thereafter and, if the cow is milked during that period, the chlorine residue may find its way into the milk and constitute a health hazard. It is thus deemed desirable to avoid the use of chlorinated compounds in products which are consumed or may come into contact with human tissues, as many of them decompose and the chorine that is liberated can combine with organic agents to form carcinogens. As a consequence, there is a need for effective anti-microbial agents for the specific use of washing or dipping the udders of cows, which agents are based on active ingredients other than chlorine.

It is, therefore, a primary object of my invention to provide anti-microbial agents for cleansing the udders and teats of dairy cows, which agents are not based on the use of a chlorine composition as an active ingredient thereof.

It is another object of my invention to provide antimicrobial agents for cleansing and sanitizing the udders and teats of cows, which agents, if some residue thereof does find its way into the human food supply, will be harmless to humans.

SUMMARY OF THE INVENTION

My invention comprises the use of extracts and resins of the hop plant as sanitizing and cleansing agents for udders and teats of cows, making use of the antimicrobial and protozoicidal properties of such hop compositions and the fact that hop plant materials are manifestly lacking in harm to humans.

DETAILED DESCRIPTION OF THE INVENTION

Hops and compounds present in hops have been used for human consumption for centuries, and the anti-microbial properties of hops, without any attendant harm to humans, make it an ideal complete or partial replacement for chlorine-based products now in use in udder cleaning preparations.

Hops, whose botanical name is *Humulus lupulus*, is a vine belonging to the botanical family of Cannabiaceae. It is grown for use in beer in many countries, and in the United States predominantly in the Western states of Washington, Oregon, Idaho and California. Female hop plants bear flowers with cone-like structures that contain so-called yellow glands. These glands constitute about 20 to 30 percent of the weight of the hop flower, and contain the hop resins that are active, anti-microbial agents. While hops are still used in beer by adding the dried, whole flowers to the beer wort and boiling the wort in order to extract the hop resins, at present various materials are available to the brewer to accomplish this purpose. Hops are extracted by solvents to obtain hop extracts that contain the essential ingredients of the hop flowers. Solvents used are ethanol or supercritical carbon dioxide.

These hop resins, also known as bitter resins or bitter acids, comprise various fractions and compounds, such as humulone, which is the so-called alpha resin; lupulone, which is known as the beta resin; xanthohumol, and a large number of minor compounds. Most of these compounds and resins, most notably lupulone, humulone and xanthohumol, exhibit antimicrobial activity. Upon heating in aqueous solution, many of these compounds are changed into their iso forms that have increased water solubility and are also antimicrobial.

Hops and hop-derived extracts and resins are commercially available from S. S. Steiner, Inc., of New York, N.Y., as are preisomerized extracts and some of the above-named compounds, per se and in their iso forms. In addition, certain reduced compounds and chemically prepared derivatives can be obtained, for example, a tetrahydroisoalpha resin. Still other trace constituents are mentioned in the voluminous hop literature.

Much research has been conducted on the preservation properties of hop resins since Holy Hildegarde, of Bingen, Germany, first discovered hop activity for the preservation of beer and use in the fermentation process during the early Middle Ages. It is known that hop constituents are active against gram-positive bacteria, and that they have good activity against Staphylococci, Streptococci, and also against the acid fast Mycobacteria that cause tuberculosis. Recently, hop resins have been found to be active against *Listeria monocytogenes*, the causative bacteria of Listeriosis.

Some of these microorganisms against which hop resins are active, are important agents in mastitis, and are also causative of human diseases derived from milk. From the results of tests that have been conducted, it is clear to me that hop resins, which are natural agents that have a history of centuries of consumption by humans without ill effects, are ideally suited to eliminate pathogens in udder care. Beyond their use in the dairy industry, hop resins are also applicable to the treatment of mastitis in women as well as farm animals other than cows, and for pets, or wherever mastitis may occur.

With regard to specific udder washes and dips, it is recognized that hop compounds, e.g., lupulone or humulone, will be utilized in concentrations that are effective to kill pathogenic targets, although where there are multiple target pathogens, it may be found beneficial to utilize other bactericides as well. The wash and dip compositions may also employ surface active agents to assist in the uniform distribution of the liquid over the udder area being treated, as well as the usual agents useful in preserving the texture of the udders and teats and their protection from chafing or other injury. Following are some examples of compositions that are effective in washing or dipping the udders of dairy cows to markedly reduce bacterial infection. All of the hop compounds referenced are commercially available from S. S. Steiner, Inc., of New York, N.Y.

EXAMPLE I

A preparation of 5 liters of udder treatment solution was formed by adding 125 mg. of lupulone, the beta resin, to two liters of water, thoroughly stirring, and then adding 25 grams of sodium lauryl sulfate, a surfactant, and 250 grams of glycerol to the mixture. After vigorous stirring the lupulone was dispersed or dissolved throughout the solution Then sufficient water was added to make up 5 liters of solution, and agitation was continued to preserve the continuity of the dispersion or solution. The solution was then suitable for direct application to the udders and teats of dairy cows by spraying, dipping or other prosaic means.

EXAMPLE II

A preparation was formed in the same manner as that of Example I, except that tetrahydroisohumulone was used in lieu of lupulone. The mixture was also suitable for application to the udders and teats of dairy cows.

EXAMPLE III

Another preparation was formed in the same manner as that of Example I, except that xanthohumol was utilized instead of lupulone. While the xanthohumol is somewhat less soluble in water than the alpha or beta resins, sometimes referred to as bitter acids, the resulting composition was also suitable for application to the udders and teats of dairy cows.

Other Examples

Similar udder and teat washes were formulated as described in Examples I, II, and III, but the preisomerized forms of the alpha and beta resins, as obtained from S. S. Steiner, Inc., were utilized. As these iso forms of the resins are more water-soluble than the resins per se, the solutions were made up without the necessity of using a surfactant as a dispersing agent. These solutions that do not include a surfactant are deemed advantageous because they reduce the foaming that accompanies most surfactant use and the possibly deleterious effect of the surfactant on the tender skin of the animal. The use of buffers may also be advantageous in some cases.

While preliminary work has revealed the unique efficacy of hop compounds as antibacterial agents useful in washing and dipping the udders of dairy cattle, it will be apparent that the precise, optimum levels of these ingredients, either in their normal or iso forms have not yet been determined. Further experimentation will doubtless show that certain hops resins have advantages over others, or that the preisomerized forms have advantages at specific concentrations. Thus, while it is presently believed that an aqueous solution in a concentration of about 0.2 to 100 mg. of hops $\alpha$ and/or $\beta$-resins per liter of solution is an effective range, with a narrower range of 10 to 50 mg. per liter being preferable, subsequent research will enable an optimum range to be determined for any particular hop compound or a combinations of hop compounds.

As a consequence, I consider my invention to be general in scope rather than the discovery of specific ranges of specific hops compounds, but the use of hops extracts and resins generally as udder and teat washes and dips. My use of the term, hop compounds, in the accompanying claims is intended to include, inter alia, hop extracts and resins in both their standard and iso forms, as well as other forms of these hop compounds, e.g., hydrogenated hop compounds such as tetrahydoisohumulone and xanthohumol.

It will be apparent to those of skill in this art that many alterations and modifications of the specific embodiments of my invention described hereinbefore will be obvious, such as the use of a variety of emollients and surfactants,. As to these alterations and modifications, it is desired that they be included within the purview of my invention, which is to be limited only by the scope, including equivalents, of the following, appended claims.

I claim:

1. A method of sanitizing the udders and teats of dairy cows, comprising washing or dipping said udders and teats with an aqueous solution an active ingredient of which is a hop compound in a concentration effective to kill pathogens on said udders and teats without causing trauma to said cows.

2. A method as claimed in claim 1, in which said pathogen is a susceptible bacterium.

3. A method as claimed in claim 1, in which said hop compound is lupulone.

4. A method as claimed in claim 1, in which said hop compound is humulone.

5. A method as claimed in claim 1, in which said hop compound is the iso form of humulone.

6. A method as claimed in claim 1, in which said hop compound is selected from the group consisting of hydrogenated iso forms of lupulone and humulone and combinations thereof.

7. A method as claimed in claim 6, in which said hop compound is tetrahydroisohumulone.

8. A method as claimed in claim 1, in which said hop compound is xanthohumol.

* * * * *